United States Patent [19]
Ackley et al.

[11] Patent Number: 5,489,988
[45] Date of Patent: Feb. 6, 1996

[54] ENVIRONMENTAL SENSOR AND METHOD THEREFOR

[75] Inventors: Donald E. Ackley, Lambertville; Michael Krihak, Kenilworth, both of N.J.; Chan-Long Shieh, Paradise Valley, Ariz.

[73] Assignee: Motorola, Schaumburg, Ill.

[21] Appl. No.: 368,502

[22] Filed: Jan. 3, 1995

[51] Int. Cl.$^6$ ............................ G01N 21/00; G02B 6/00
[52] U.S. Cl. ........................ 356/436; 356/440; 422/82.11; 385/12; 250/227.11; 250/573
[58] Field of Search ...................................... 356/244, 410, 356/411, 440, 441, 436, 300, 409, 39, 412, 73, 432, 433, 434, 435; 422/57–58, 82.06, 82.07, 82.11; 385/12, 13; 250/573–576, 227.11, 227.14

[56] References Cited

U.S. PATENT DOCUMENTS

| | | | |
|---|---|---|---|
| 3,110,816 | 11/1963 | Kaisler et al. | 385/12 |
| 5,300,564 | 4/1994 | Avnir et al. | 422/57 X |
| 5,314,829 | 5/1994 | Coles | 422/58 |

OTHER PUBLICATIONS

Ding et al., "Fibre Optic pH Sensors Prepared by Sol–Gel Immobilisation Technique" Electronic Letters, vol.27, No. 17, Aug. 15, 1991, pp. 1560–1562.

MacCraith eet al., "LED–Based Fiber Optic Oxygen Sensor Using Sol–Gel Coating", Electronics Letters, vol. 30, No. 11, May 26, 1994, pp. 888–889.

*Primary Examiner*—Frank Gonzalez
*Assistant Examiner*—K. P. Hantis
*Attorney, Agent, or Firm*—Robert F. Hightower

[57] ABSTRACT

A sensor (10,30,40,50,70) for detecting chemicals and changes in the surrounding environment utilizes a sol-gel sensor element (14,16,17,54,56,57) containing a chemical indicator. Grooves (12,13,24,52,53) are formed in a substrate (11,51). The grooves are filled with a sol-gel material having a chemical indicator, and the sol-gel is cured to adhere to the substrate (11,51). The grooves (12,13,24,52, 53) are formed to facilitate optically coupling a fiber optic cable (46) to the sol-gel sensor element. Light is coupled from the fiber optic cable (46) to the sol-gel sensor element (14,16,17,54,56,57).

28 Claims, 4 Drawing Sheets

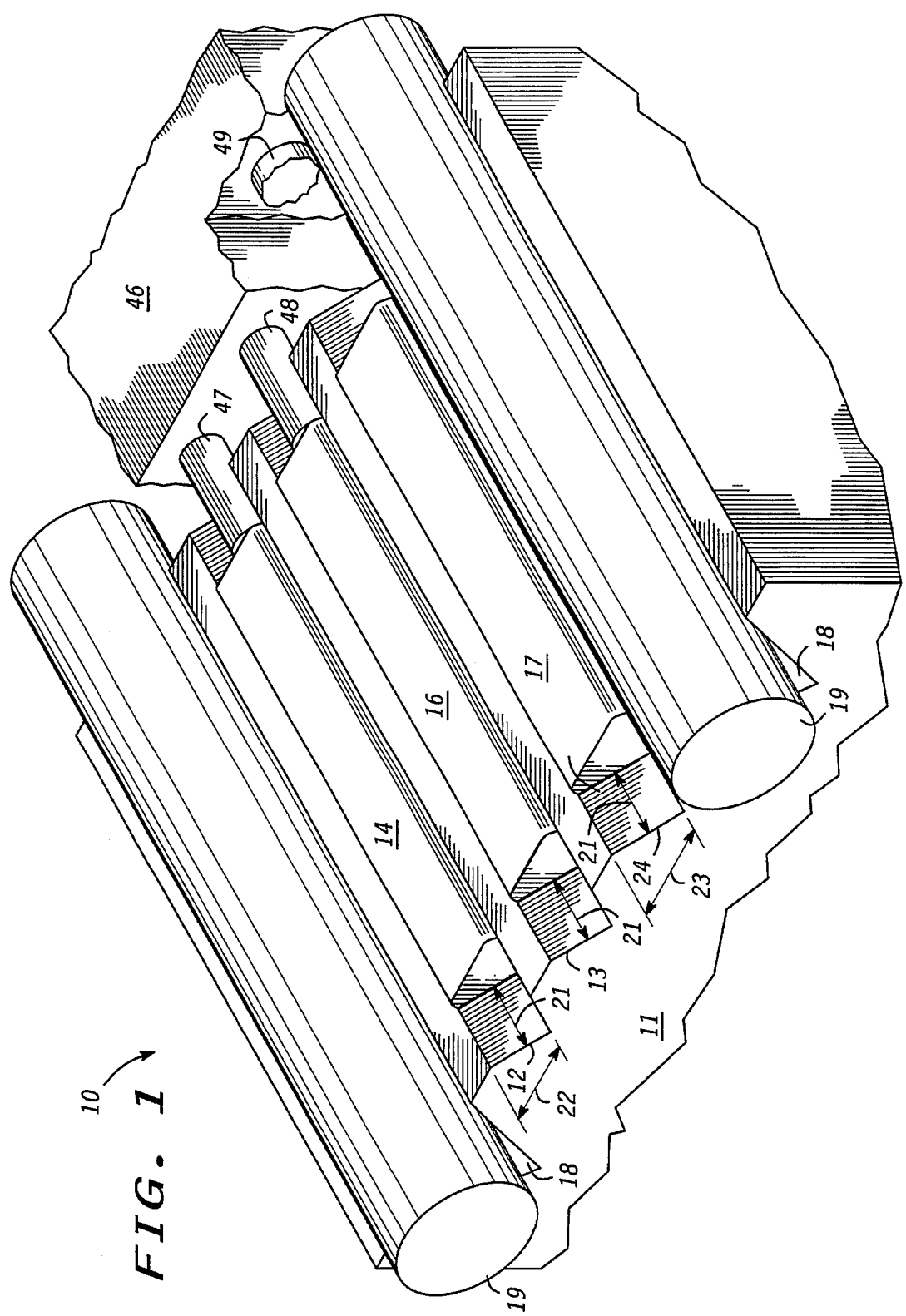

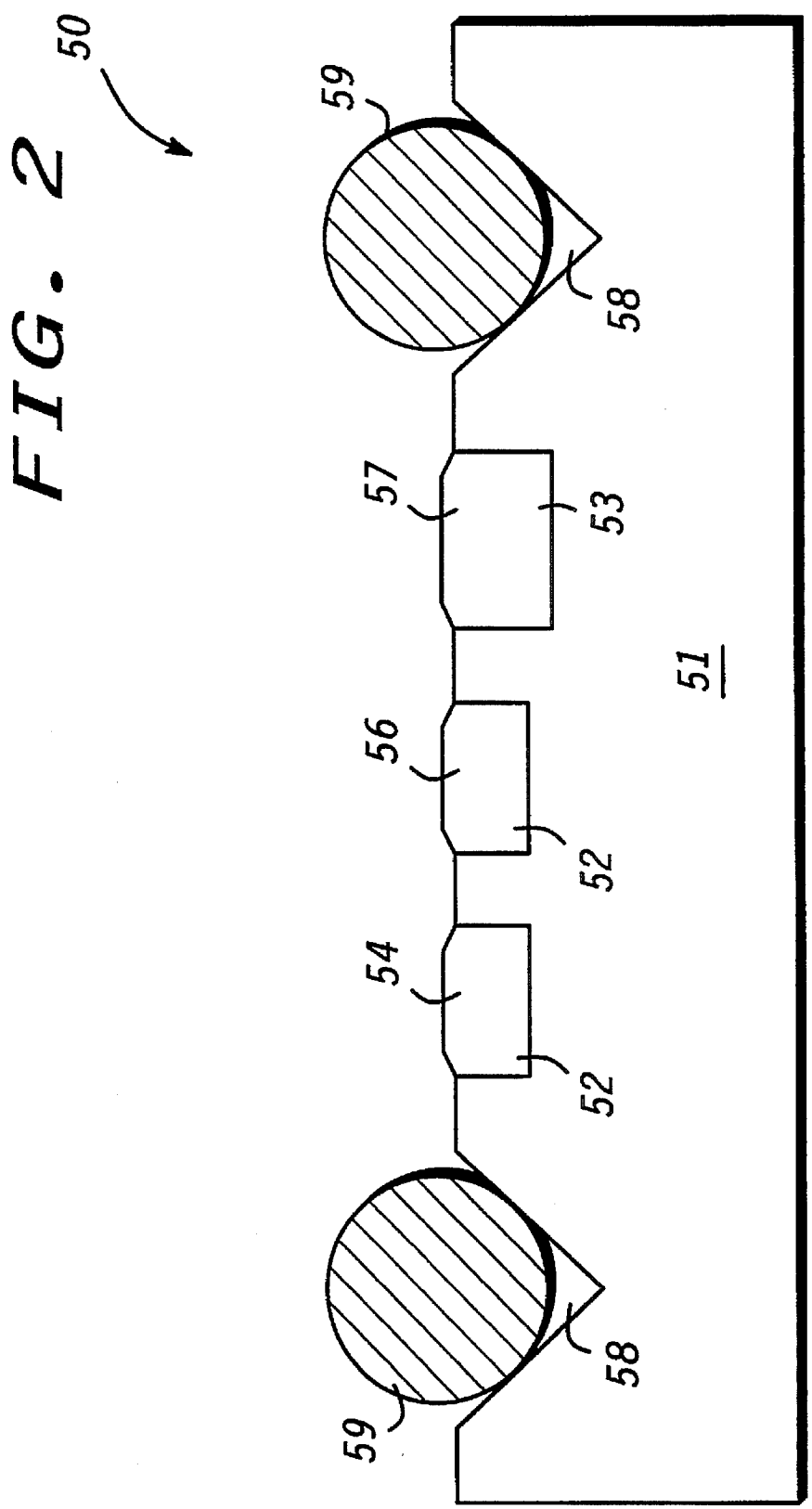

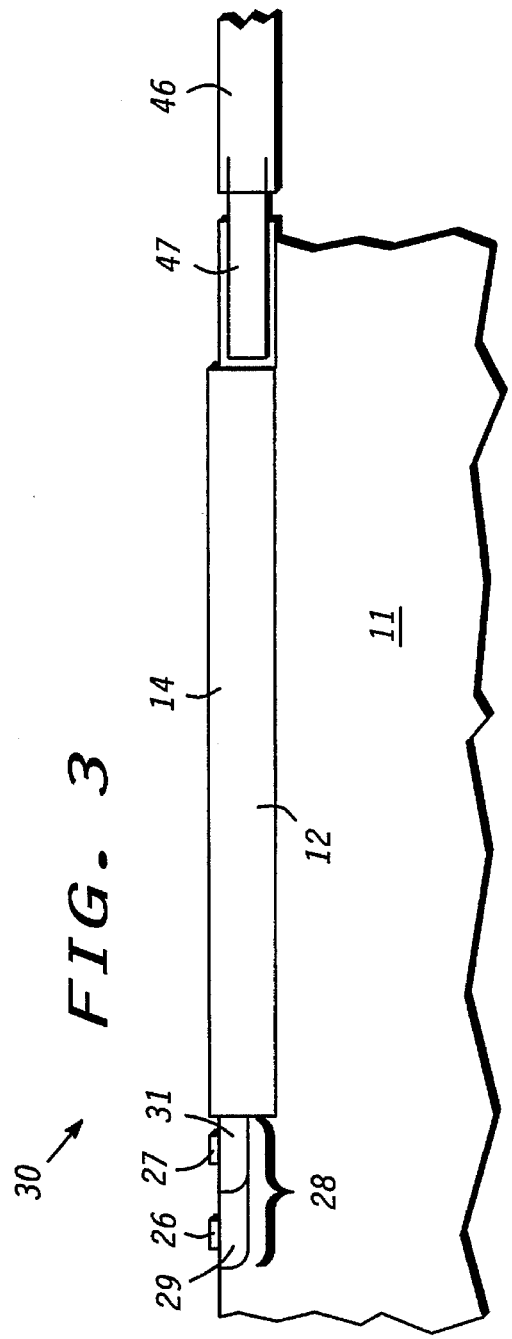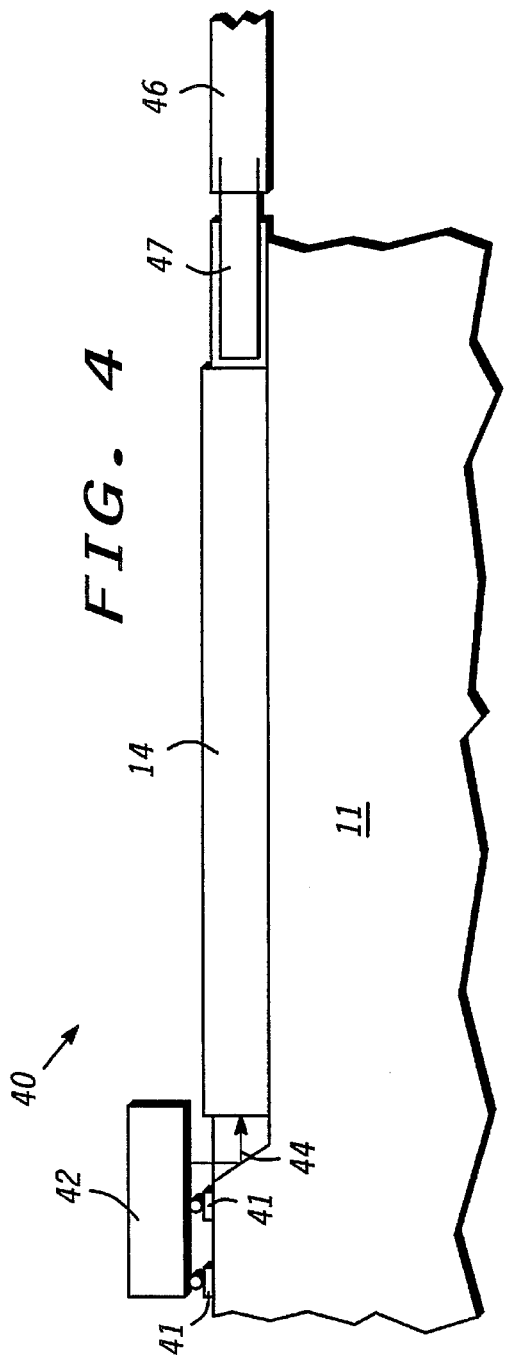

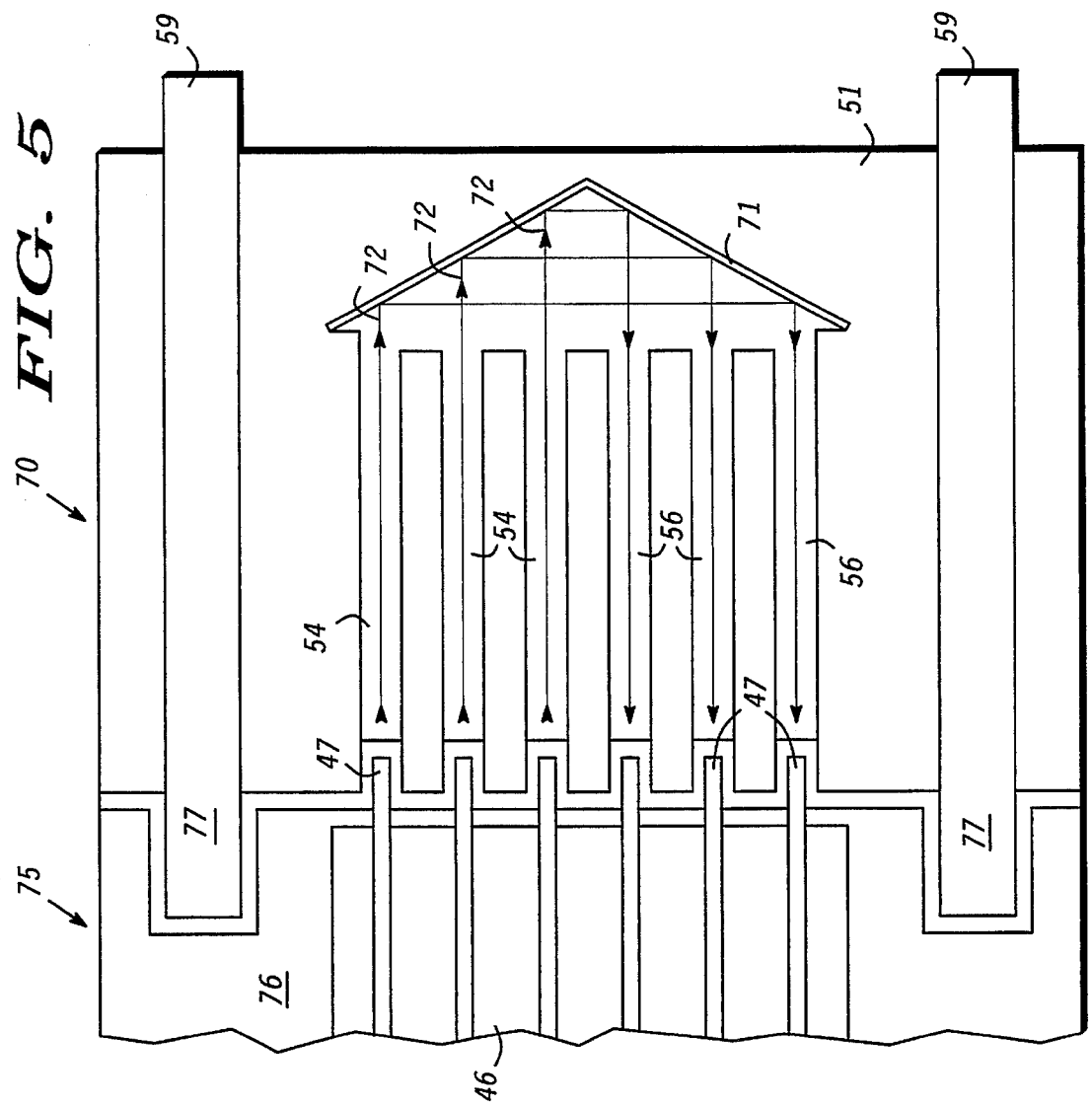

ENVIRONMENTAL SENSOR AND METHOD THEREFOR

BACKGROUND OF THE INVENTION

The present invention relates, in general, to sensors, and more particularly, to a novel optical sensor.

Glass fiber optic cables have previously been used as pH sensors and to detect the presence of chemicals such as carbon dioxide, carbon monoxide, and ammonia. A small section of the cladding on a cladded fiberoptic cable is removed to expose a small section of the fiber. A sol-gel derived silica glass containing a chemically sensitive dye is prepared and applied to the outside of the exposed fiber so that light does not pass through or contact the silica glass containing the chemically sensitive dye. When exposed to different levels of the chemical analyte, the transmissive capability of the fiberoptic cable is altered thereby changing the light that passes through the cable.

One problem with the prior sensors is the manufacturing cost. A portion of the cladding must be removed in a central portion of the cable, and then the sol-gel is applied to the cylindrical cable portion that is exposed. Removing the cladding and applying the sol-gel is a labor intensive, thus, expensive operation. Additionally, it is difficult to control the thickness and uniformity of the sol-gel coating. Consequently, the response time of the sensor varies according to the thickness of the sol-gel coating. Furthermore, it is difficult to produce an array of multiple sensors suitable for sensing multiple chemicals and elements.

Accordingly, it is desirable to have an optical sensor that is easy to manufacture, that has a low manufacturing cost, that has a well controlled response time, and that can easily be formed into an array of multiple sensor elements.

BRIEF DESCRIPTION OF THE DRAWINGS

FIG. 1 illustrates a perspective view of an optical sensor in accordance with the present invention;

FIG. 2 illustrates a cross-sectional elevation of an alternate embodiment of an optical sensor in accordance with the present invention;

FIG. 3 illustrates a cross-sectional elevation of another embodiment of an optical sensor having optical devices in accordance with the present invention;

FIG. 4 illustrates a cross-sectional elevation of another embodiment of an optical sensor having optical devices in accordance with the present invention; and FIG. 5 illustrates a cross-sectional plan view of another embodiment of an optical sensor in accordance with the present invention.

DETAILED DESCRIPTION OF THE DRAWINGS

FIG. 1 illustrates a perspective view of an environmental sensor or optical sensor 10 that has an array of optical sensor elements. Sensor 10 is formed on a substrate 11, for example silicon, on which a plurality of parallel V-shaped grooves, such as a first groove 12, a second groove 13, and a third groove 24, are formed on a surface of substrate 11. Grooves 12, 13, and 24 are formed by etching techniques that are well known to those skilled in the art. When silicon having a <100> orientation is utilized, the etching results in the V-groves having walls with an angle of approximately 54.7°. Within grooves 12, 13, and 24, are formed a first sol-gel sensor element 14, a second sol-gel sensor element 16, and a third sol-gel sensor element 17, respectively. Elements 14, 16, and 17 include a hydrolyzed sol-gel material formed by hydrolyzing a silica gel, such as tetraethylorthosilicate or methyltrimethoxysilane, with an alcohol and water, and optionally a catalyst such as hydrochloric acid. Methods for hydrolyzing sol-gels are well known to those skilled in the art. Typically, a mask is applied to the surface of substrate 11, and patterned to form openings exposing the portion of grooves 12, 13, and 24 in which elements 14, 16, and 17 are to be formed. The mask is removed, and the sol-gel mixture is prepared and hydrolyzed. After the hydrolysis, a chemical indicator is added to the sol-gel mixture, and the mixture is applied to the surface of substrate 11 by spin coating or other techniques that result in a uniform application. The chemical indicator typically is a dye that is sensitive to analytes that are to be measured or sensed in the environment to which sensor 10 is exposed. The sol-gel is dried completing elements 14, 16, and 17 in grooves 12, 13, and 24 respectively.

In operation, light is injected into one or a plurality of elements 14, 16, and 17. The chemical indicator in elements 14, 16, and 17 reacts with the surrounding environment and transforms the light that is passing through elements 14, 16, and 17. The effect on the light depends on the type of indicator in elements 14, 16, and 17 and the interaction between the indicator and the surrounding environment. After exposure to an atmospheric chemical to be sensed, the absorption of the indicator at a certain light wavelength typically is changed so that the intensity of light exiting elements 14, 16, and 17 is different from the light entering the elements. Other types of indicators absorb the incoming light and use the absorbed energy to emit a specific light wavelength so that the light exiting elements 14, 16, and 17 is determined by the emission frequency of the chemical indicator. Such indicators typically are referred to as operating in a fluorescence mode. Some typical indicators, the mode of operation, and the element being sensed are listed in the table below:

| Indicator | Mode | Sensing |
| --- | --- | --- |
| fluorescein | Fluorescence | oxygen,Humidity,pH |
| bromocresol Green | Absorption | pH |
| bromocresol Purple | Absorption | ammonia,ph |
| Ru(bpy)$^{2+}$ | Fluorescence | oxygen |
| Ru(ph2phen)3$^{2+}$ | Fluorescence | oxygen |
| cobalt Chloride | Absorption | humidity |
| porphyrin | Absorption | heavy metals, ammonia,pH. |

Typically, light is injected into elements 14, 16, and 17 utilizing a fiber ribbon cable 46 having individual optical conduits or fibers such as a first optical fiber 46, a second optical fiber 48, and a third optical fiber 49. The length of elements 14, 16, and 17 is typically the length of substrate 11 to provide for optically coupling to fibers 47, 48, and 49, respectively. Although a space 21 may remain between an end of elements 14, 16, and 17 and the end of each groove 12, 13, and 24, respectively, it is desirable that space 21 be as small as possible to provide optimum coupling to fibers 47, 48, and 49. The size of space 21 in FIG. 1 is exaggerated for simplicity of the drawing and the explanation.

The depth of grooves 12, 13, and 24 is selected to provide the most efficient optical coupling to fibers 47, 48, and 49. Typically, the depth is formed to provide either single mode or multi-mode operation within elements 14, 16, and 17 at the wavelength of light that is to be injected into elements 14, 16, and 17. The depth of grooves 12, 13, and 24 is determined by the width at the base of the triangle formed by each groove or top of each grove because the etching results in walls at an angle of approximately 54.7°. Typically, all grooves have substantially the same width although groove 24 is shown to have a width 23 of approximately thirty-five to fifty microns to provide multi-mode operation while grooves 12 and 13 have a width 22 of approximately ten to fifteen microns to provide single mode operation.

Because of the depth of groove 24 is greater than grooves 12 and 13, element 17 can be a multi-layer sol-gel sensor element that is formed in layers by successive application and curing of the hydrolyzed sol-gel material. The sol-gel material for the bottom layers can be either dispensed or spun-on. In such a layered implementation, the bottom layer or layers can be formed without a chemical indicator while the indicator resides only in the top layer. Using different layers facilitates changing the index of refraction from the bottom to the top of element 17 to cause the mode of light transmission to gradually change from uniformly illuminating the entire element near the ends of element 17 to illuminating only the top layer. This decreases the response time of element 17 since the indicator and the light reside near the surface of element 17.

Sensor 10 also includes a plurality of alignment grooves 18 formed along outside edges of substrate 11 and parallel to grooves 12, 13, and 24. A locating pin 19 within each alignment groove 18 is used to align an external connector, as described hereinafter in FIG. 5, to sensor 10 so that optical fibers, such as fibers 47, 48, and 49, are optically coupled to elements 14, 16, and 17 as will be explained hereinafter in FIG. 5. Each pin 19 typically has a length that is greater than a length of substrate 11 to facilitate mating with the external connector.

By etching the V-grooves into substrate 11, grooves 12, 13, and 24 have very smooth walls that facilitate elements 14, 16, and 17 functioning as low loss waveguides for light passing through elements 14, 16, and 17. Since semiconductor etching techniques are utilized, grooves 12, 13, and 24 and sensor elements 14, 16, and 17 always have the same shape and are easily formed into large arrays to facilitate multi-channel operation. Utilizing spin coating of the sol-gel further enhances the repeatability and manufactureability of sensor 10. Furthermore, spin coating allows laminating layers to vary the index of refraction of the optical sensor elements and to allow for forming thick sensor elements for multi-mode operation.

Forming an array of multiple optical sensor elements allows forming one element without a chemical indicator to function as a reference channel to optimize sensitivity and stability of sensor 10. Furthermore, using an array of elements facilitates using a different chemical indicator in each element so that sensor 10 can detect a variety of chemicals or conditions in the surrounding environment. Additionally, the chemical indicator can be omitted and sensor 10 can function as a connector for coupling together two fiber ribbon cables.

FIG. 2 is a cross-sectional illustration of an optical sensor 50 that is another embodiment of sensor 10 shown in FIG. 1. Sensor 50 has a molded substrate 51 that is molded from plastic or other suitable material. Substrate 51 is molded with a first plurality of grooves 52 that function similarly to grooves 12 and 13 shown in FIG. 1, and a deeper groove 53 that functions similarly to groove 24 shown in FIG. 1. Groves 52 and 53 can have various shapes since groves 52 and 53 are molded, but are square in the preferred embodiment. Alignment grooves 58 that function similarly to grooves 18 (FIG. 1) are also formed when substrate 51 is molded. Subsequently, a first sensor element 54, a second sensor element 56, and a third sensor element 57 that function similarly to elements 14, 16, and 17 (FIG. 1), respectively. Elements 54, 56, and 57 typically are formed by dispensing the sol-gel into groves 52 and 53 instead of spinning-on coating. Locating pins 59, function similarly to locating pins 19 shown in FIG. 1.

FIG. 3 illustrates a cross-sectional portion of an optical sensor 30 that is an alternate embodiment of sensor 10 shown in FIG. 1. Elements of FIG. 3 that have the same reference numbers as FIG. 1 are similar to the corresponding FIG. 1 elements. Sensor 30 has optical devices that are formed in substrate 11 and optically coupled to sensor element 14. An optical detector 28 is formed in substrate 11 adjacent to a first end of element 14. Detector 28 has an anode 29 and a cathode 31 so that detector 28 may detect light that has been injected into element 14 by fiber 47. Bonding pads 26 and 27 are provided to form electrical contact to anode 29 and cathode 31, respectively. Fiber 47 is coupled to a second end of element 14.

By using a substrate material that is compatible with forming optical emitters, sensor 30 could also include optical emitters coupled to the second end of element 14 in place of fiber 47. For example, using a gallium arsenide substrate 11, a light emitting diode could be used as a emitter, or using a gallium arsenide with an epitaxial growth as substrate 11, a laser emitter could be formed along with the detector. For FIG. 4 illustrates a cross-sectional portion of an optical sensor 40 that is another embodiment of optical sensor 10 shown in FIG. 1. Elements of FIG. 4 that have the same reference numbers as FIG. 1 are similar to the corresponding FIG. 1 elements. Although explained relative to FIG. 1, sensor 40 also could be another embodiment of sensor 50 shown in FIG. 2. Sensor 40 has an optical device 42 optically coupled to a first end of element 14. Device 42 could be an optical detector for sensing light injected into element 14 by fiber 47 or could be an optical emitter for injecting light 44, illustrated by an arrow, into element 14 for coupling to fiber 47. Device 42 typically is attached to bonding pads 41, on a surface of substrate 11, by solder bump or other techniques that are well known to those skilled in the art. In order to couple light 44 into or out of element 14 and device 42, device 42 is positioned so that light 44 reflects off of the slanted wall of V-grove 12 (FIG. 1), thus, the slanted end wall of V-groove 12 functions as a mirror for light 44. Alternately, device 42 could be an edge emitting emitter with the emission area coupled to element 14 or device 42 could be mounted on an electrical substrate such as a printed circuit board that is attached to bonding pads 41.

The embodiments shown in FIG. 3 and FIG. 4 facilitate manufacturing the sensors with light sources and detectors thereby reducing labor and lowering the costs of such sensors. This allows the formation of a more compact sensor that is readily interfaced to electronic readout circuitry. Additionally, costs of fiber ribbon cable is reduced with sensor 30 (FIG. 3) and sensor 40 (FIG. 4).

FIG. 5 illustrates a cross-sectional plan view of an optical sensor 70 that is an alternate embodiment of sensor 50 shown in FIG. 2. Elements of FIG. 5 that have the same reference numbers as FIG. 2 are similar to the corresponding FIG. 2 elements. Substrate 51 has a prism 71 molded into substrate 51. Prism 71 is near a first end of each sensor element 54 and 56, and optically coupled to the first end of each element 54 and 56. An optical connector 75 includes a fiber ribbon cable 46 having a plurality of optical fibers 47 that are optically coupled to sensor elements 54 and 56. A portion of fibers 47 inject light into elements 54 as shown by arrows 72, the light exits elements 54, enters prism 71 where it is internally reflected and coupled back to corresponding elements 56, and coupled into corresponding fibers 47, as shown by arrows 72.

Connector 75 has a connector body 76 attached to cable 46 to hold cable 46 firmly in place. Typically, body 76 is a molded plastic that is molded around cable 46. Connector 75 also has alignment openings 77 aligned to pins 59 for receiving pins 59. Cable 46 is positioned relative to pins 59 prior to molding so that fibers 47 align with elements 54 and 56. It should be noted that connector 75 is also suitable for use with sensor 10 (FIG. 1), sensor 50 (FIG. 2), sensor 30 (FIG. 3), and sensor 40 (FIG. 4). Additionally, the chemical indicator can be omitted from the embodiments shown in FIG. 3, FIG. 4, and FIG. 5 to facilitate using sensors 30, 40, and 50 as compact optical steering devices or electro-optic devices.

Prism 71 facilitates the implementation of a single fiber ribbon cable thereby reducing the size and corresponding cost of a sensor system.

By now it should be appreciated that a novel sensor has been provided. Forming grooves by etching or by molding facilitates accurate placement and low manufacturing costs. Spinning-on the sol-gel and indicator material results in accurate control of the thickness with corresponding fast response time, highly repeatable sensor elements, and low manufacturing costs. Additionally, etching or molding the groves, and spinning-on the sol-gel and indicator facilitates forming arrays of indicators in a small area that can be used to sense a variety of chemicals and conditions in the environment.

We claim:

1. An environmental sensor comprising:
    a substrate having a surface;
    a plurality of parallel grooves on the surface; and
    a sol-gel sensor element in each groove of the plurality of parallel grooves.

2. The sensor of claim 1 further including at least one sol-gel sensor element having a chemical indicator.

3. The sensor of claim 2 wherein the chemical indicator is one of fluorescein, bromocresol green, bromocresol purple, $Ru(pby)^{2+}$, or $Ru(Ph_2phen)_3^{2+}$.

4. The sensor of claim 2 wherein each sol-gel sensor element has a different chemical indicator.

5. The sensor of claim 1 further including an optical device optically coupled to a first end of each sol-gel sensor element of the sol-gel sensor element in each groove of the plurality of parallel grooves.

6. The sensor of claim 5 further including an optical device optically coupled to a second end of each sol-gel sensor element of the sol-gel sensor element in each groove of the plurality of parallel grooves.

7. The sensor of claim 5 further including a plurality of bonding pads on the surface for interconnecting to the optical device coupled to the first end of each sol-gel sensor element.

8. The sensor of claim 1 further including a fiber ribbon cable having a plurality of optical fibers aligned to the plurality of parallel grooves so that an end of each sol-gel sensor element is optically coupled to the plurality of optical fibers.

9. The sensor of claim 1 further including a plurality of alignment grooves and a locating pin within each alignment groove, the locating pin having a length that is greater than a length of the substrate.

10. The sensor of claim 9 further including a connector body housing a fiber ribbon cable having a plurality of optical fibers, the connector body having an alignment opening aligned to the locating pin so that an end of each sol-gel sensor element is optically coupled to the plurality of optical fibers.

11. The sensor of claim 1 wherein the substrate is a molded plastic material and the plurality of parallel grooves are molded into the molded plastic material.

12. The sensor of claim 11 further including a prism molded into the substrate near a first end of each sensor element, the prism optically coupled to the first end of each sensor element for receiving light from a first sol-gel sensor element of the sol-gel sensor element in each groove and reflecting light into a second sol-gel sensor element of the sol-gel sensor element in each groove.

13. The sensor of claim 1 wherein each sol-gel sensor element has a chemical indicator.

14. An environmental sensor comprising:
    a silicon substrate having a surface;
    a plurality of parallel V-shaped grooves on the surface; and
    a sol-gel sensor element in each groove of the plurality of parallel V-shaped grooves, at least one sol-gel sensor element having a chemical indicator.

15. The sensor of claim 14 further including an alignment V-groove and a locating pin within the alignment V-groove, the locating pin having a length that is greater than a length of the silicon substrate.

16. The sensor of claim 14 wherein the chemical indicator is one of fluorescein, bromocresol green, bromocresol purple, $Ru(pby)^{2+}$, or $Ru(Ph_2phen)_3^{2+}$.

17. The sensor of claim 16 wherein each sol-gel sensor element has a different chemical indicator.

18. The sensor of claim 14 wherein the plurality of parallel V-shaped grooves have a width of approximately 10 to 50 microns at a top of each groove.

19. The sensor of claim 14 further including an optical device optically coupled to a first end of each sol-gel sensor element.

20. The sensor of claim 19 wherein the optical device is an optical emitter, and further including an optical detector optically coupled to a second end of each sol-gel sensor element.

21. The sensor of claim 20 wherein the optical emitter and the optical detector are formed in the silicon substrate.

22. The sensor of claim 20 wherein the optical emitter and the optical detector are attached to the surface of the silicon substrate.

23. The sensor of claim 19 wherein an end of a groove of the plurality of V-shape grooves functions as a mirror for reflecting light for optically coupling the optical device to the first end.

24. A method of forming a sensor comprising:
    forming a substrate having a plurality of grooves in a surface of the substrate; and
    forming a sol-gel sensor element within each groove of the plurality of grooves, at least one sol-gel sensor element having a chemical indicator.

25. The method of claim 24 further including forming alignment grooves parallel to the plurality of grooves and positioning a locating pin within each alignment groove.

26. The method of claim 24 wherein forming the sol-gel sensor element within each groove includes spinning a hydrolyzed sol-gel material containing the chemical indicator into each groove then curing the hydrolyzed sol-gel material.

27. The method of claim 24 wherein forming the sol-gel sensor element within each groove includes forming a multi-layer sol-gel sensor element by successive application and curing of a sol-gel material.

28. The method of claim 27 wherein the chemical indicator resides only in a single layer of the multi-layer sol-gel sensor element.

* * * * *